(12) United States Patent
Katsuda et al.

(10) Patent No.: US 7,275,931 B2
(45) Date of Patent: Oct. 2, 2007

(54) MEDICAL IRRADIATION APPARATUS

(75) Inventors: Naoki Katsuda, Kyoto (JP); Haruo Ogawa, Kyoto (JP); Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 391 days.

(21) Appl. No.: 10/839,469

(22) Filed: May 5, 2004

(65) Prior Publication Data

US 2004/0248059 A1    Dec. 9, 2004

(30) Foreign Application Priority Data

May 6, 2003   (JP)  ............................. 2003-128360
May 27, 2003  (JP)  ............................. 2003-149724

(51) Int. Cl.
*A61C 3/00*   (2006.01)
*A61N 5/06*   (2006.01)

(52) U.S. Cl. .......................................... 433/29; 607/88
(58) Field of Classification Search ................ 433/29; 607/88–94; 362/109, 119
See application file for complete search history.

(56) References Cited

U.S. PATENT DOCUMENTS

| | | | | |
|---|---|---|---|---|
| 5,485,316 A * | 1/1996 | Mori et al. | ................. | 359/708 |
| 5,843,143 A * | 12/1998 | Whitehurst | ................... | 607/88 |
| 6,193,386 B1 * | 2/2001 | Reynolds | ..................... | 362/109 |
| 6,331,111 B1 * | 12/2001 | Cao | ............................ | 433/29 |
| 6,692,251 B1 * | 2/2004 | Logan et al. | ................. | 433/29 |
| 6,709,128 B2 * | 3/2004 | Gordon et al. | ............... | 362/119 |
| 2002/0151941 A1 * | 10/2002 | Okawa et al. | ................ | 607/99 |
| 2003/0036031 A1 * | 2/2003 | Lieb et al. | ..................... | 433/29 |

* cited by examiner

*Primary Examiner*—John J Wilson
(74) *Attorney, Agent, or Firm*—Koda & Androlia

(57) ABSTRACT

A medical irradiation apparatus comprising a main body, a luminous body comprised of a light emitting element provided in a light outlet of the main body, an annular reflective member with a reflective surface provided at the circumference of the luminous body, the reflective surface reflecting the light from the luminous body forward, and a lens member provided so as to cover a forward opening of the reflective member, the lens member refracting and transmitting the direct light from the luminous body and the light reflected from the reflective member. According to the apparatus, all the outgoing light from the lens member is emitted so as to direct into a specified irradiation area.

29 Claims, 15 Drawing Sheets

MEDICAL IRRADIATION APPARATUS

BACKGROUND OF THE INVENTION

1. Field of the Invention

The present invention relates to a medical irradiation apparatus and more particularly to improvement of a medical lighting installation such as a hardening apparatus of prosthetic photo polymerization resin, an intraoral lighting installation and the like in the dental treatment field.

2. Prior Art

In dental treatment, there used are a photo polymerization device for rapidly hardening the prosthetic photo polymerization resin in a tooth, an irradiation device, being attached to several kinds of handpieces or individually, for irradiating an objective tooth for treatment in the oral cavity, a dental light (shadowless light) standing at the side of a treatment bed for irradiating the oral cavity, and the like. Such a light is required to condense the light in a narrow oral cavity and is different from the light used in other fields which is required to illuminate wide area.

Halogen lamp and a xenon lamp have been used as the light source of the above-mentioned irradiation device. Recently used is a light emitting element which has characteristics of a long operating life and little electric power consumption comparing with those lamps like LED (light emitting diode), a semiconductor laser, and so on. Such a light emitting element like a LED and a semiconductor laser is provided in the form of a mounting device sealing a naked chip cut out of a wafer in a case or in the form of a bear chip.

In case of the above-mentioned irradiation device, more particularly photo polymerization device, for dental use, it is required to be high power for reducing the irradiation time in addition to condense the light on a small area because of its characteristics. Further, because it is used in a small area like the oral cavity, it is desired to be small, light weight, and compact.

The above-mentioned light emitting element like LED and a semiconductor laser is designed to distribute light in a wide area, so that it is commonly applied in other field which is required to be widely illuminated, however, the illumination intensity per a unit area in the irradiation field is small. Because the output per one element is small, the number of light emitting elements may be increased in order to obtain a desired light volume, however, it goes against the requirement of downsizing. The applicant of the present invention has proposed a medical irradiation device for solving the conflicting problems of high power and downsizing in JP-A-2002-306512 and JP-A-2002-360605.

The medical irradiation device disclosed in those prior arts uses plural light emitting elements and applies a light condensing means or improves the shape of a light introduction means is improved in order to effectively use the light emitted from each light emitting element, thereby enabling irradiation with a large light volume per a unit area. Its practical value has been highly evaluated. Although the light emitting element doesn't generate heat as a single body, if plural elements are used, its heat generation isn't ignored. Such a heat generation isn't preferable to a dental irradiation device which often contacts with gum and cheek, so that a cooling means is further provided for cooling the light emitting element in the prior arts.

According to the above-mentioned medical irradiation apparatus, it isn't considered that the photo polymerization device for hardening the prosthetic photo polymerization resin filled in a tooth forms the beam pattern which uniformly irradiates light from the surface to the deeper area of prosthetic resin. Therefore, those inventions are not enough in the sight of effectively and homogenously hardening resin and a drastic improvement is required. Further, the medical irradiation apparatus disclosed in the above-mentioned prior art has achieved high power and downsizing and also has taken a measure for preventing heat generation. Therefore, its practical use has been highly evaluated, however, the following problems have been pointed out. Namely, the above-mentioned cooling means mainly acts on the substrate of the light emitting element, and it doesn't actively cool the front (light emitting side) of the light emitting element, the light condensing means, or the light introduction means. Accordingly its cooling effect has not bee enough. Specifically, because the light condensing means and the light introduction means which are provided at the front of the light emitting element often contact with gum, there causes an obstacle for medical treatment if heat generation of these means is restrained enough.

SUMMARY OF THE INVENTION

The present invention is proposed in order to solve the above-mentioned problems and provides a new medical irradiation apparatus capable of high power and downsizing in which an irradiation light is advantageously used for a desired purpose and heat generation is efficiently restrained.

The first object of the present invention is to effectively utilize the outgoing light in a treatment target area by setting the shape of an annular reflective member and a lens member in such a manner that almost all the outgoing light from the lens member is emitted to a specified irradiation area, thereby executing an objective treatment effectively and accurately. Further, the light diverging laterally from the light emitting element constituting the luminous body is reflected forward by the annular reflective member, so that the reflection light is also directed to irradiate on the area to be reflected, thereby effectively utilizing the luminous ability of the light emitting element. Therefore, high power is obtained without arranging many light emitting elements and downsizing is achieved. In addition, the luminous body is protected with the lens member, thereby preventing contamination and damage.

The above-mentioned specified area is formed substantially cylindrical around the optical axis of the outgoing light, the distribution of the illumination intensity in the field area in each irradiation field orthogonal to the optical axis in the irradiation area is substantially uniform, and the illumination intensity in any irradiation fields is almost the same. In case of hardening the prosthetic photo polymerization resin in the tooth, homogenous and rapid hardening is carried out by positioning the tooth surface in the specified area. Accordingly, the combination of the shape of the annular reflective member and the shape of the lens member makes possible that the distribution of the illumination intensity in each irradiation field in a specified area is made substantially uniform and the illumination intensity in each irradiation filed is made substantially the same.

The second object of the invention is, in addition to the above, to supply air in the space area surrounded with the luminous body, the reflective member and the lens member to actively cool down and to effectively restrain the light outlet from generating heat. As a result, the apparatus becomes highly applicable to a dental irradiation apparatus wherein heat generation in the oral cavity is highly problematic and the duration against heat of the light emitting element is improved. Further, by introducing a cooling gas into the space area, cloud generated in the lens member is prevented, so that there is no fear of reducing illumination intensity during operation. In addition, even an irradiation apparatus having priority in high power like a dental lights and other medical shadowless light is effectively cooled down with the cooling means, thereby enabling to provide plural rows of light emitting elements.

The annular reflective member is preferably formed as a rotationally symmetrical object around its central axis, the distal opening for irradiation is more enlarged than its base portion, like a horn more specifically, the section of the reflective surface along its central axis is preferably linear, concave or convex. If the section of the reflective surface along its center axis is concave, the concavely curved line is preferably defined by an oval arc or a continuous plural straight lines. According to the annular reflective member provided with such a reflective surface, particularly the light diverging laterally from the luminous body is reflected into the lens member, so that the light emitted from the luminous body is efficiently used to achieve high power. In addition, the reflection light is easily condensed into a narrow area and the irradiation density in the irradiation field becomes large.

When the section of the reflective surface along its center axis is concavely curved, the concavely curved line is defined by a part of a parabola and the tangent line of the parabola where the annular reflective member and the lens member are incorporated agrees with an optical path line of the most external irradiation light among the irradiation light directly pointed to the lens member from the luminous body. According to such construction, almost all of the light emitted from luminous body enters into the lens member.

The lens member is preferably comprised of a glass lens which is rotationally symmetrical around the central axis thereof and the light entering side thereof is formed convex, and the light emitting side thereof is formed flat, or convexly curved, convex, or substantially flat. Further, the light entering side of the lens member is preferably formed as a curved surface at a center and continuous inclined surfaces therearound. The curved surface is spherical with a small curvature radius, whereas the inclined surface is substantially linear in the section along the central axis of the lens member. Thus the lens member is comprised of a glass lens, it is highly hygienic as a dental irradiation apparatus which is inserted and used in the oral cavity. Further, the central curved surface is spherical with a small curvature radius, the beam directly entering into and emitting out of the central curved surface from the luminous body is condensed with a uniform light volume at the area to be irradiated in the irradiation area. In addition, the direct light from the luminous body and the reflection light from the reflective member at the inclined surfaces therearound are also uniformly refracted and emitted therefrom, thereby being condensed with a uniform light volume at the area to be irradiated.

The light entering side and/or light emitting side of the lens member is preferably provided with an anti-reflection film coating (AR coat) or with a water repellent or oil repellent coating. Such a coating makes the entering light into or outgoing light from the lens member efficiently direct to a specified area without reflecting on the light entering side or the light emitting side. In addition, contamination by prosthetic photo polymerization resin, saliva or oil is prevented, thereby keeping uniform light volume required for photo polymerization.

As mentioned above, appropriately determining the shape of the annular reflective member and the lens member, almost all of the outgoing light from the lens member is emitted to a specified irradiation area. More specifically, most preferable combination is that the annular reflective member in which the section of the reflective surface is concave like an oval arc and the lens member in which the central curved surface is spherical with a small curvature radius and the section of the inclined surface therearound is substantially linear.

When such a combination is used for hardening the prosthetic photo polymerization resin in the tooth, if the specified irradiation area is a space area where the distance from the light emitting end of the light outlet is 1 to 12 mm and of which the irradiation field diameter is 5 to 12 mm, the space area corresponds to the prosthetic area of the photo polymerization resin. Therefore, the illumination intensity (irradiation density) per a unit area in the prosthetic area becomes large to be uniformly irradiated, so that hardening of the prosthetic photo polymerization resin is rapidly and homogenously developed from the surface to the deeper area.

If the distance from the light emitting end is less than 1 mm, a prosthetic photo polymerization resin or saliva is easily attached on the light emitting end, thereby causing contamination. If the distance from the light emitting end is larger than 12 mm or the diameter of the irradiation field exceeds 12 mm, the illumination intensity per a unit area required for photo polymerization tends not to be obtained and the uniformity of the illumination intensity in the irradiation field is apt to be reduced. Therefore, the hardening of the prosthetic photo polymerization resin becomes slow and homogenous hardening isn't carried out. In addition, if the diameter of the irradiation field is less than 5 mm, the irradiation apparatus is required to be moved if there is a prosthetic photo polymerization resin at the area wider than the irradiation field, so that homogenous hardening of the prosthetic photo polymerization resin isn't desired.

The reflective member and the lens member are desirably detachable to the light outlet by means of a screw type cap member, by which their aright attachment to the light outlet is performed via an O-ring. If the reflective member and the lens member are thus detachable, an individual sterilization with an autoclave is possible after removing these members. Further, they may be replaced with other members with different condensing characteristics depending on an intended purpose, thereby achieving diversified treatment. Still further, they are airtightly and integrally attached via the O-ring, so that when the space area surrounded with the luminous body, the reflective member and the lens member is cooed with a cooling air, efficient cooling is carried out without leaking the cooling air.

The main body of irradiation apparatus desirably constitutes a handpiece which is held and handled with a hand or fingers and the light outlet is formed at the tip end portion of the main body. Accordingly, this apparatus of the present invention is applied to a dental handpiece inserted into the oral cavity. Operator holds the main body of irradiation apparatus, inserts the tip end portion in the oral cavity, moves the light outlet near a treatment target region, makes the luminous body illuminate, thereby hardening the prosthetic photo polymerization resin in the tooth and irradiating the tooth to be treated. Therefore, hardening of the prosthetic photo polymerization resin in the back teeth, which has been difficult with the conventional photo polymerization apparatus, becomes facilitated.

Being detachable to the base portion of the handpiece as mentioned above, the main body of irradiation apparatus may be removed out of the base portion of the handpiece to be subjected in sterilization with an autoclave or to be replaced with other main body of irradiation apparatus depending on the condition of the treatment region. Further, if the base portion is formed as a coupling of an air turbine handpiece and the coupling is provided with a connector for supplying/exhausting air for driving a turbine and a power source connecting terminal, by exchangeably connecting the main body of the air turbine handpiece and the main body of irradiation apparatus, both of them are commonly used. Namely, a connection port into the air supply pipe and the exhaust pipe for cooling and the power connecting terminal are provided for the base end of the main body of irradiation apparatus and are enable to be connected with the connector for supplying/exhausting air for driving a turbine and the power source connecting terminal in case of connecting with the coupling, thereby serving a compression air for driving a turbine as the cooling air and serving the power source as the power source for the luminous body. Further, the air supply pipe and the exhaust pipe are provided in the handpiece, a rotary flow of the cooling gas in the air supply pipe and the exhaust pipe gets the handpiece cool down, thereby causing no trouble for operator's manipulation.

If a cordless irradiation apparatus is constructed such that the power source and the control part are housed in the main body of irradiation apparatus, such an apparatus is used at any places and is easily used for home bleaching. Further providing a cooling medium, the base portion of the air supply pipe is designed to be connected to the air supply means (such as a fan) provided in the main body of irradiation apparatus and the power source and the control part are housed in the main body of irradiation apparatus, thereby executing drive control of the light emitting element and the air supply means by means of the power source and the control part.

The light emitting element is preferably a bear chip or an integrated wafer provided with plural bear chips on a substrate. These bear chips are desirably molded with a transparent resin at the light emitting side thereof. These bear chips are LED chips or semiconductor laser chips. The bear chip cut out of the wafer is small, so that small and high-power luminous body may be easily formed by integrating plural bear chips.

The luminous body comprised of a light emitting element (for example a blue LED) for radiating light with wavelength (the peak wavelength is 430-480 nm) suitable for hardening the photo polymerization resin or the luminous body comprised of a light emitting element for radiating white light may be applied in this invention. The former is used for hardening the prosthetic photo polymerization resin and the latter is used as a light for the treatment region. The light outlet provided with each one of these two kinds of luminous bodies may be detachable to the main body of irradiation apparatus and may be exchangeably used. Or these two kinds of luminous bodies may be provided for the main body of one irradiation apparatus and the irradiation light may be selected by switching operation of a switch. Such a selective use of two kinds of luminous bodies contributes efficiency of dental treatment.

The reflective member has desirably an air supply communication bore for communicating between the air supply pipe and the space area and an exhaust communication bore for communicating between the space area and the exhaust pipe, and a cooling gas from the air supply pipe is introduced in the space area via the air supply communication bore and is discharged from the exhaust pipe via the exhaust communication bore. According to such construction, the cooling gas from the air supply pipe always moves along a series of the rotary flow; the air supply communication bore→the space area→the exhaust communication bore→the exhaust pipe. While staying in the space area, the cooling gas is directly injected on the front surface of the luminous body (light emitting element), the reflective surface of the reflective member, the inside of the transparent member through the annular reflecting member as piping, thereby effectively cooling each member.

It is preferable that a heat sink is further provided in to the back of the support body of the luminous body, the back of the support body and the heat sink are provided in the exhaust pipe and the support body is constructed by a substrate of the light emitting element. A small metal plate with a small specific heat such as aluminum is used as the heat sink. Further, the substrate is a ceramic substrate, an alumina substrate, an insulation coated metal substrate, and the like. The heat sink is thus attached to the support body of the luminous body, namely the substrate of the light emitting element, so that the luminous body is cooled down from its back. Further, because the substrate and the heat sink are provided in the exhaust pipe to be exposed in the cooling gas flow, the substrate is cooled down with the cooling gas and the heat stored in the heat sink is sequentially discharged, thereby being preferably used to discharge the heat of the substrate.

BRIEF DESCRIPTION OF THE DRAWINGS

FIG. 4a shows the sectional view of an essential part wherein the section of the reflective surface along the center axis is concavely curved and the concavely curved line is defined by an oval arc, in FIG. 4b the section of the annular reflective member is convexly curved and the convexly curved line is defined by a part of parabola, in FIG. 4c the section of a reflective surface is concavely curved and the concavely curved line is defined by continuous plural straight lines.

FIG. 5a shows a pattern when light is directly entered into the lens member, FIG. 5b shows a pattern when the reflection light from the annular reflective member is entered into the lens member, and FIG. 5c shows when both patterns are occurred (actual irradiation pattern).

FIG. 6 is a graph showing the measured data of the relative illumination intensity (%) at the position which is 5 mm distance from the light emitting end in case of FIG. 4a.

FIG. 8a shows its plane view and FIG. 8b shows the vertical section along the line Y-Y in FIG. 8a.

FIG. 13a is its outline view and FIG. 13b is the partial enlarged view.

DETAILED DESCRIPTION OF THE INVENTION

Figure 1:
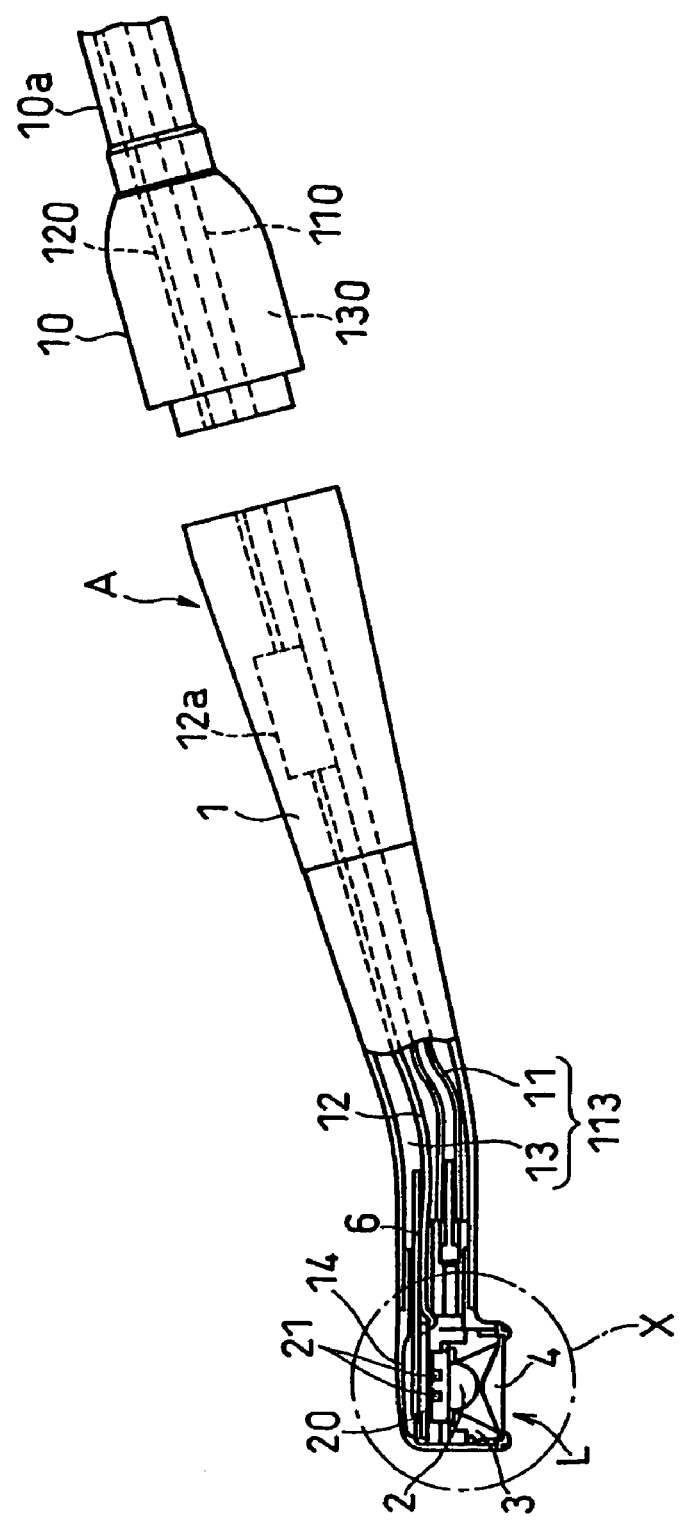
FIG. 1 is a partially broken appearance showing one embodiment in which the medical irradiation apparatus of the present invention is applied to a handpiece type dental photo polymerization apparatus.
Figure 2:
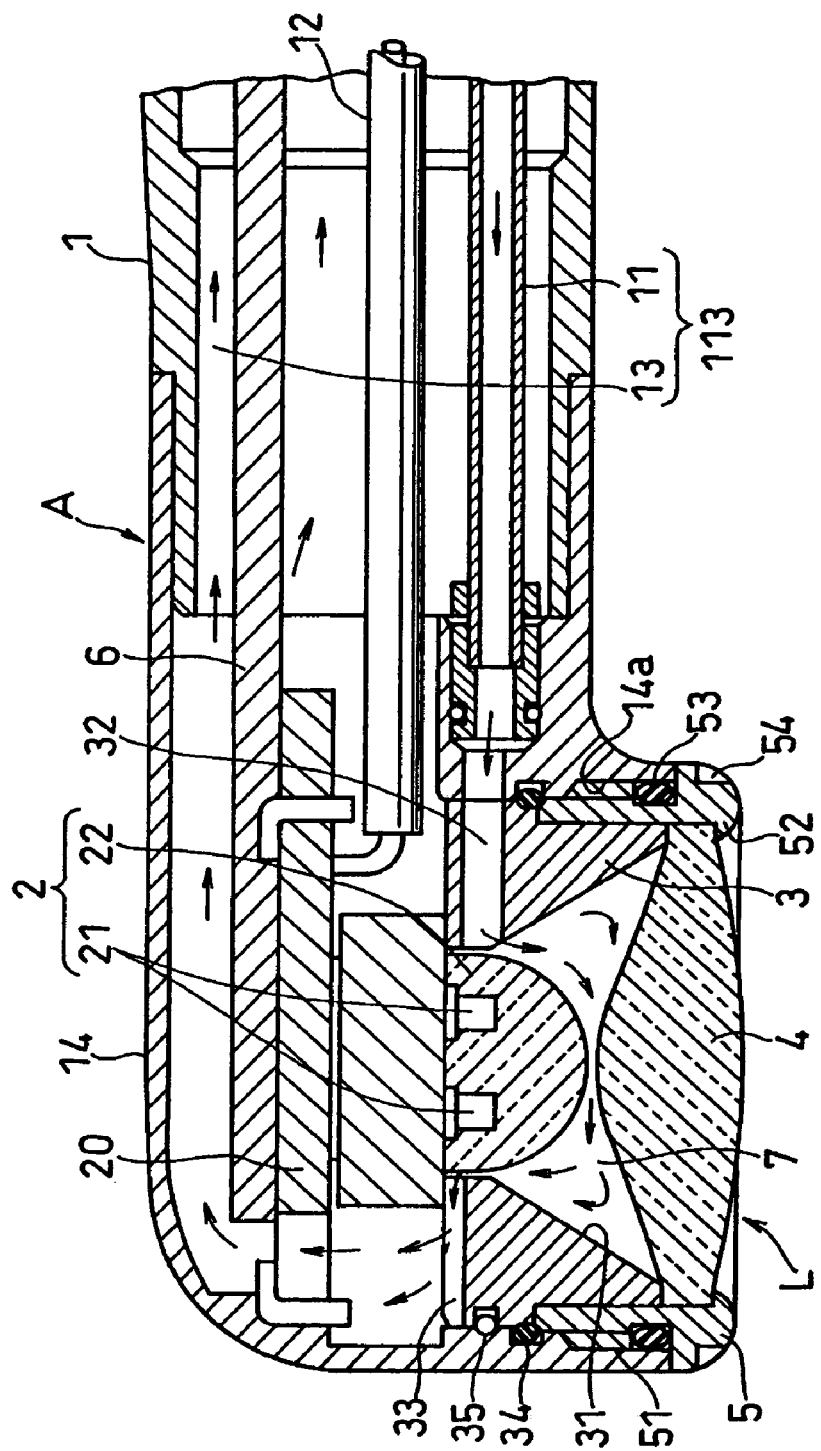
FIG. 2 is an enlarged view of the part "X" in FIG. 1.

FIG. 1 and FIG. 2 show an embodiment in which the medical irradiation apparatus of the present invention is applied to a handpiece type dental photo polymerization apparatus A. The reference numeral 1 is a handpiece body (main body of irradiation apparatus) and is detachable to a base portion 10. A hose 10a housing a supply pipe 110 of compression air, a power cord 120, and an exhaust pipe 130 is connected to the base portion 10. The exhaust pipe 130 is defined by the space other than the supply pipe 110 and the power cord 120 in the hose 10a. The supply pipe 110 for compression air is connected to a compressor as an air supply means, not shown, provided in a dental treatment room and the power cord 120 is connected to a power source.

The base portion 10 of the handpiece constitutes a coupling to the handpiece body 1 such that when the base portion 10 is connected to the base end of the handpiece 1, the supply pipe 110 of compression air, the power cord 120 and the exhaust pipe 130 are connected to an air supply pipe 11, a power cord 12 for a luminous body and an exhaust pipe 13, they are explained later, respectively in the handpiece body 1.

The handpiece base 10 may be an exclusive coupling for the photo polymerization apparatus A, however, it may be also used for an air turbine handpiece. If the main body of an air turbine handpiece housing pipes for an air turbine and a working medium, not shown, is constructed so as to be detachable to the handpiece base 10, they are exchangeably used, thereby improving efficiency of treatment and space saving.

The handpiece body 1 is formed tubular so as to be held and operated with an operator's hand and the air supply pipe 11, the power cord 12 for a luminous body and the exhaust pipe 13 are housed therein. The exhaust pipe 13 is formed of the space other than the air supply pipe 11 and the power cord 12 for a luminous body in the handpiece body 1 and is communicated from the tip end portion to the base end therein. A cooling means 113 is comprised of the air supply pipe 11 and the exhaust pipe 13. A control part 12a is provided in midstream of the power cord 12 for a luminous body to execute on-off control of the luminous body 2 (light emitting element), mentioned later, by means of a hand switch or a foot switch, not shown, through the control part 12a.

A cylindrical light outlet 14 is formed at the tip end portion of the handpiece body 1 in such a manner the opening of the light outlet 14 directs to be orthogonal to the longitudinal direction of the handpiece body 1 and a luminous unit L is provided in the light outlet 14. The luminous unit L is comprised of a modularized luminous body 2, an annular reflective member 3 provided around the luminous body 2, and a lens 4 provided so as to cover the forward opening of the annular reflective member 3. The luminous body 2 is comprised of plural light emitting elements 21 . . . such as blue LED chips (bear chip) mounted on a substrate (support body) 20 and a transparent resin mold 22 which covers the light emitting element 21 . . . like a dome to be integrated. The power cord 21 for the luminous body is electrically connected to a circuit (not shown) formed on the substrate 20. Thus, the luminous body 2 is constructed as a bear chip or as an integrated wafer formed such that plural bear chips are provided on the substrate, and further, the light emitting side of the bear chip is molded with a transparent resin, so that plural bear chips are integrated because they are small, thereby easily achieving small and high-power luminous body.

The annular reflection body 3 is made of a metal member or a resin member like a bugle, the inner reflective surface 31 of which is enlarged toward its front end and the reflective surface 31 is mirror finished or evaporation finished with silver in order to improve the reflexivity. If the annular reflective member 3 is made of metal (for example, aluminum or stainless), the heat release function is achieved, thereby obtaining effect of preventing heat generation of the luminous body 2.

The annular reflective member 3 is provided so as to surround the dome-shaped resin mold 22 of the luminous body 2 attached in the light outlet 14. Communication bore 32 for air supply is provided for thus provided annular reflective member 3 so as to meet the forward end of the air supply pipe 11 housed in the handpiece body 1 and to communicate the inside of the reflective member 3 into the air supply pipe 11.

At opposite position, an exhaust communication bore (groove) 33 is formed so as to communicate the inside of the reflective member 3 and the exhaust pipe 13. The reflective member 3 is desirably provided with a globule 35 capable of rising and setting in its radius direction (a concave part for receiving the globule 35 is required in the space of the light outlet 14) or a positioning means such as a marking in order to ensure the agreement of the air supply communication bore 32 and the forward end of the air supply pipe 11.

The lens 4 is made of glass or hard transparent resin (such as acryl resin). In case of the dental photo polymerization apparatus A for use in the oral cavity like the present embodiment, the lens 4 is preferably a glass lens from a hygienic point of view. This lens 4 is attached so as to cover the forward opening of the annular reflective member 3. Integration of the annular reflective member 3 and the lens 4 into the light outlet 14 is achieved by a ring-shaped screw cap 5. Such integration will be explained hereinafter.

The annular reflective member 3 is positioned in such a manner that the air supply communication bore 32 agrees with the forward end of the air supply pipe 11 as mentioned above and is inserted into its cylindrical space from the opening side of the light outlet 14. A first O-ring 34 is provided around the annular reflective member 3 and elasticity of the O-ring 34 acting between the outer face of the annular reflective member 3 and the inner face of the space of the light outlet 14 prevents the annular reflective member 3 from unexpectedly falling off and rattling in thrust direction.

Next, the lens 4 is attached to the forward opening of the annular reflective member 3, then the ring-shaped screw cap 5 is engaged to be integrated into the light outlet 14 from the opening through a male screw 51 formed with threads therearound and a female screw 14a formed with grooves in the space of the light outlet 14. Inward brim 52 is formed at the tip opening of the cap 5 and is designed to be stopped at the peripheral circumference of the lens 4, so that when the cap is screwed to be integrated with the light outlet 14, the annular reflective member 3 and the lens 4 are incorporated and integrated without causing rattling.

The reference numeral 53 indicates a second O-ring and is elastically loaded between the outer face of the cap 5 and the inner face of the light outlet 14 when the cap 5 is thus screwed and integrated, thereby preventing loosening of the cap 5 and exerting sealing function in the light outlet 14. The reference numeral 54 is a notch for acting a tool for attaching and detaching the cap 5.

Heat sink 6 comprised of a small metal plate with small specific heat such as aluminum is fixed to the back of the substrate 20 of the luminous body 2 with a screw (not shown). The heat sink 6 extends into the base end of the handpiece body 1 and the heat sink 6 and the back of the substrate 20 are provided in the exhaust pipe 13.

When the prosthetic photo polymerization resin in a tooth is hardened with the dental photo polymerization apparatus A thus incorporated with the luminous unit L, the tip end of the light outlet 14 is approached to an objective region of the tooth (about 2-5 mm) and the switch of the luminous body 2 is turned on. The light emitted from the light emitting element 21 is transmitted through the resin mold 22 and through the lens 4 and is irradiated on the objective region of the tooth.

The light diverging laterally from the luminous body 2 is reflected on the reflective surface 31 of the annular reflective member 3 and the reflection light also passes through the lens 4 and is irradiated on the objective region of the tooth. Therefore, the light radiated from the light emitting element 21 is made good used for hardening the prosthetic photo polymerization resin. Therefore, high-power irradiation ability is obtained without modularizing plural light emitting elements 21.

In this case, the light emitting element 21 is preferably driven by pulse. Because of the pulse driving, the hardening speed of photo polymerization resin is easily controlled depending on the size and cycle of the pulse. For example, high-power light is instantaneously irradiated on the photo polymerization resin to obtain large polymerization depth. When the photo polymerization resin is contracted by instantaneously irradiating a large volume of light, the light volume is gradually increased by pulse driving to prevent the resin from contracting by rapid change in the light volume. If a light emitting element is used, such a pulse driving is useful.

In parallel with irradiation, a compression air is introduced as a cooling gas from the air supply pipe 11 into the space boundary 7 formed with the luminous body 2, the annular reflective member 3 and the lens 4 through the air supply communication bore 32 like arrows shown in the figure. Thus introduced compression air stays in the space boundary 7, then is exhausted out of the apparatus through the exhaust communication bore 33 and the exhaust pipes 13 and 130. With such a series of the compression air flow such as; the air supply pipe 11→the air supply communication bore 32→the space area 7→the exhaust communication bore 33→the exhaust pipe 13, the resin mold 22 of the luminous body 2, the annular reflective member 3, the lens 4, the substrate 20 and the heat sink 6 are always cooled down to prevent heat generation from the light outlet 14 and the handpiece body 1.

The heat sink 6 is integrated with the substrate 20 and absorbs heat of the substrate 20. The heat sink 6 is always exposed to the above-mentioned compression air flow and the absorbed heat is sequentially released by the cool air, thereby keeping its cooling function. The inside of the lens 4 is always exposed to the compression air flow, so that it is always cooled down to prevent generation of cloud and prevent reduction of the illumination intensity from the luminous body 2 during operation.

In the figure, the lens 4 and the annular reflective member 3 are detachable to the light outlet 14 by means of a screw type cap 5. They may be integrated to construct a head member so as to be detachable to the handpiece body 1. The cooling air is introduced into the space area 7 in the figure, however, only the back of the substrate 20 and the heat sink 6 may be exposed to the cooling air. In this case, it is preferable to fill a transparent resin in the space area 7 to fix these members.

The lens 4 is provided so as to cover the opening of the annular reflective member 3, so that the luminous body 2 is covered to prevent contamination and damage. Accordingly, the direct light from the luminous body 2 (light emitting element 21) and the reflection light from the annular reflective member 3 are entered in the lens 4, the light is emitted to a specified irradiation area (the area from the surface to the deep part of the prosthetic resin in case of hardening the prosthetic photo polymerization resin) when the light is transmitted and refracted through the lens 4 to be emitted. In the irradiation field of the irradiation area, the light becomes a beam which includes a large amount of parallel light as a whole and has a uniform and large illumination intensity (irradiation density) per a unit area.

Figure 3:
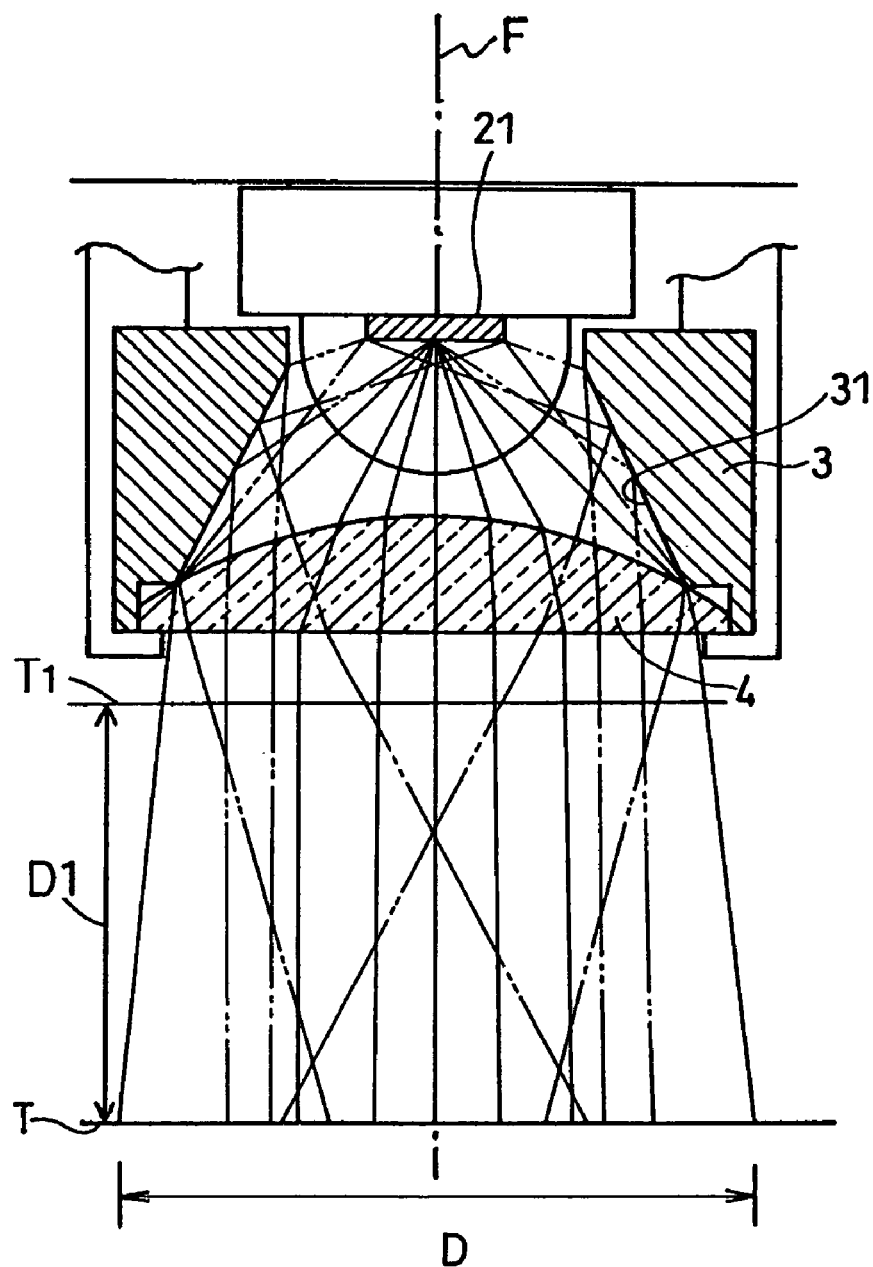
FIG. 3 is an explanatory view diagrammatically showing the radiation light emitted from a light emitting element.

FIG. 3 is an explanatory view diagrammatically showing radiation light. The figure shows an embodiment in which the reflective surface 31 of the annular reflective member 3 is enlarge into its front end and its section is linear. The lens 4 is formed such that the inner face of the luminous body 2 is a convex surface defined by a spherical surface with a large curvature radius and the light emitting side thereof is flat. In the figure, the solid line indicates an optical path which directly enters into the lens 4 from the light emitting element 21 to be transmitted therethrough, and the two-dotted line indicates an optical path which enters into the lens 4 and transmits therethrough after being reflected on the reflective surface 31 of the annular reflective member 3.

According to the photo polymerization apparatus provided with an irradiation patter as shown in FIG. 3, the distance of the light emitting end of the light outlet 14 is positioned so as to be about 5 mm from the region to be hardened (tooth surface) and the switch of the luminous body 2 is turned on when the prosthetic photo polymerization resin in the tooth is to be hardened. As shown in the figure, almost all of the outgoing light is directed to the approximately cylindrical area of which the diameter is D at the length D1 between T1 and T which are the distance from the light emitting end of the light outlet 14. In each irradiation field in the area substantially uniform and equal illumination intensity can be obtained. The diameter of the irradiation area (irradiation filed) on the tooth surface is preferably set about 8 mm. When the substantially cylindrical beam which includes a large amount of parallel light and is around the optical axis is irradiated on the prosthetic photo polymerization resin in the tooth with the irradiation pattern which is uniform with a large illumination intensity per a unit area in each irradiation field D, the irradiation light is permeated into the deep part other than the surface of the prosthetic photo polymerization resin. Thus, the prosthetic photo polymerization resin is rapidly and homogenously hardened all over and the light volume on the tooth surface is not changed even when the distance T from the region to be hardened is somewhat changed, thereby assuring homogenous hardening.

In FIG. 3, the reflective surface 31 of the annular reflective member 3 is formed as a rotationally symmetrical object around the center line F of the annular reflective member 3 and its section is linear. The reflective surface 31 may be convex or concave and its section may be circular arc, oval arc, parabola, hyperboloid, continuous plural straight lines, or the like, so that the reflection light is made to be emitted to a specified irradiation area as much as possible after the reflection light transmits the lens 4. When the reflection light is thus set to be emitted to the specified irradiation area after transmitting the lens 4, it is clear that the reflective surface 31 need not be rotationally symmetrical around the center line F of the annular reflective member 3. One example of such an annular reflective member which is not rotationally symmetrical is that combined with many small flat mirrors and that of which the section orthogonal to the center line F is oval or polygonal.

The lens 4 is preferably formed such that the inner face of the luminous body 2 is convex, the section is arc shaped as a whole (including a combination of arc with different curvatures) or the center is arc shaped and the part therearound is linearly inclined. The outer face (light emitting face) is preferably flat or convex, substantially flat. According to the combination of the shape of the annular reflective member 3 and the shape of the lens 4 (including the difference of the curvature radius of arc), it may be designed such that the specified area (depending on the intended use) is formed like a cylinder around the optical axis as shown in FIG. 3, the distribution of the illumination intensity is almost uniform in the field area of each irradiation field orthogonal to the optical axis in this irradiation area, and the illumination intensity is almost the same in each irradiation field.

Figure 4A:
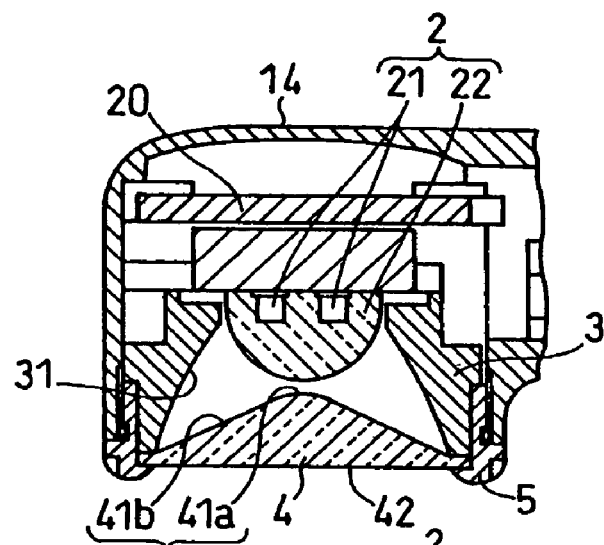
FIG. 4a, FIG. 4b, and FIG. 4c show an example of light outlet in which three kinds of annular reflective members with different shape are combined with the lens member.
Figure 4B:
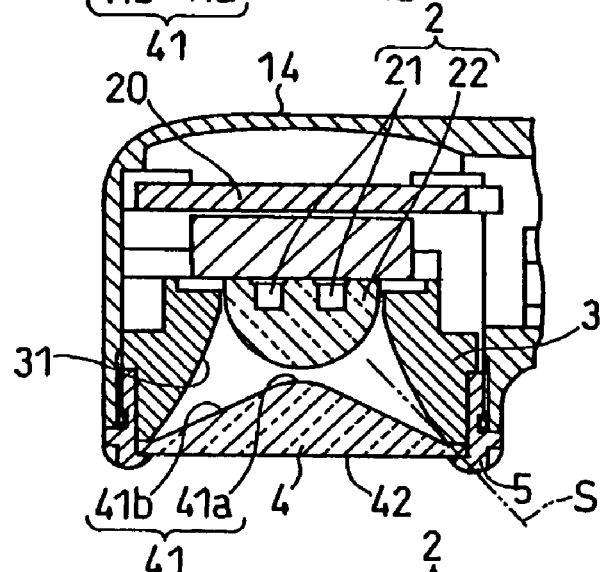
Figure 4C:
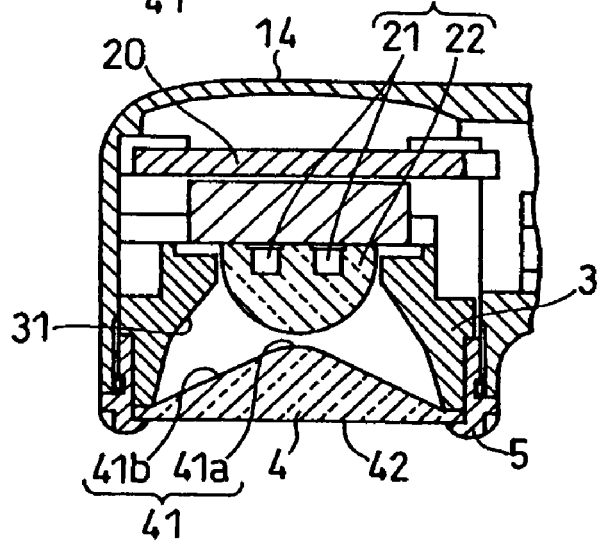

FIG. 4a, FIG. 4b, and FIG. 4c show an example of the combination of three kinds of annular reflective members 3 and the lens 4 of which the center 41a of the inner face 41 facing the luminous body 2 is an arc (spherical) with a small curvature radius and the surrounding area 41b is linearly inclined hyperboloid (non spherical). The outer face 42 at the light emitting side is flat or convex, substantially flat. In the embodiment of FIG. 4a, the section of the reflective surface 31 of the annular reflective member 3 is concave, which is formed with an oval arc. In the embodiment of FIG. 4b, the section thereof is convex, which is formed with a part of parabola. Further in the embodiment of FIG. 4c, the section of the reflective surface 31 of the annular reflective member 3 is concave, which is formed with a continuous two straight lines.

These shapes are appropriately selected depending on the conditions of the specified irradiation area (size and depth of irradiation field). In FIG. 4a and FIG. 4c, the light diverging laterally, specifically in abeam, emitted from the luminous body 2 is also reflected on the reflective surface 31 to be directed to the lens 4, so that almost all of the light emitted from the luminous body 2 is effectively used, thus achieving efficient and high power irradiation.

In FIG. 4b, the tangent S of the parabola where the annular reflective member 3 and the lens 4 are incorporated is designed to agree with the optical path line of the most external irradiation light directly pointed to the lens 4 from the luminous body 2. Therefore, almost all of the light emitted from the luminous body 2 enters into the lens 4, thereby similarly achieving efficient and high power irradiation.

Comparing the irradiation pattern at the position more than 10 mm above the light emitting end in each embodiment, the light volume is reduced in the embodiments in FIG. 4b and FIG. 4c, however, in the embodiment in FIG. 4a, it has been proved that only 30% of the light volume is reduced. Further in FIG. 4a, it has also exemplified that there causes no dark lane around the irradiation field and uniform light volume is obtained all over the irradiation field. In addition, the light including a large amount of parallel light is easily condensed on a small irradiation field and it is preferable to obtain beam with large irradiation density, thereby being most desirably used. The dark lane in this specification refers to a part which is seen to be dark because of unevenness of light volume or low light volume.

However, in the embodiments other than FIG. 4a, it has been proved that the light volume or the irradiation density at the position where the distance from the light emitting end is 3-5 mm is almost the same as that of FIG. 4a and the dark lane isn't generated at the distance. Therefore, the shapes of the annular reflective member 3 and the lens 4 are appropriately combined depending on a desired irradiation pattern, so that useful combination is suitably applied.

Figure 5A:
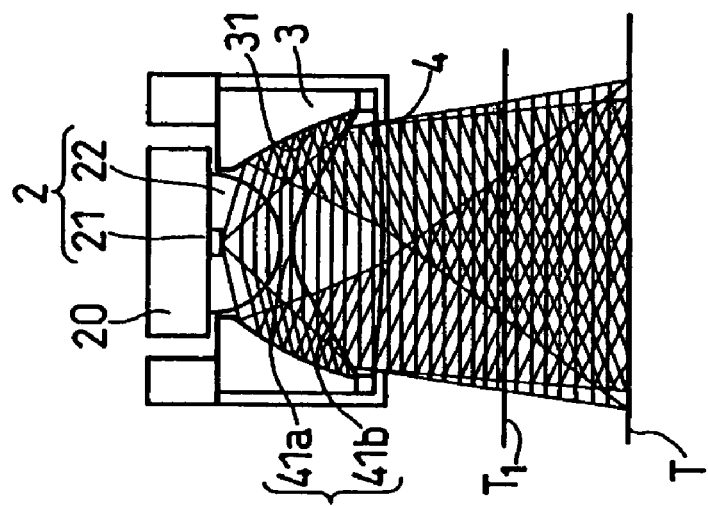
FIG. 5a, FIG. 5b and FIG. 5c are explanatory views in which the irradiation pattern shown in FIG. 4a is decomposed.
Figure 5B:
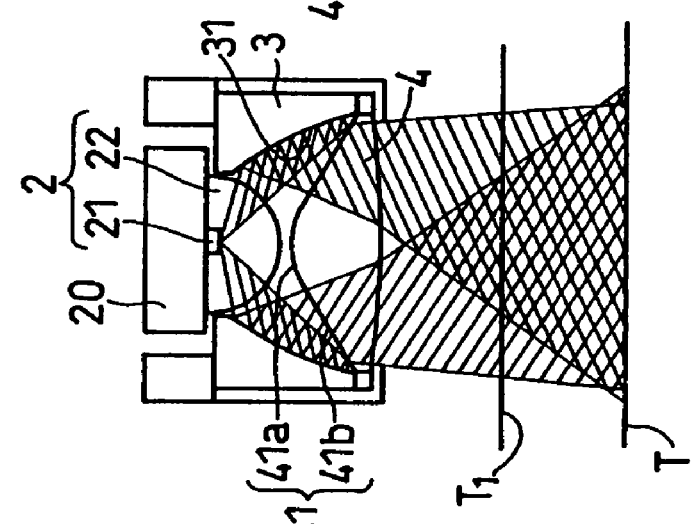
Figure 5C:
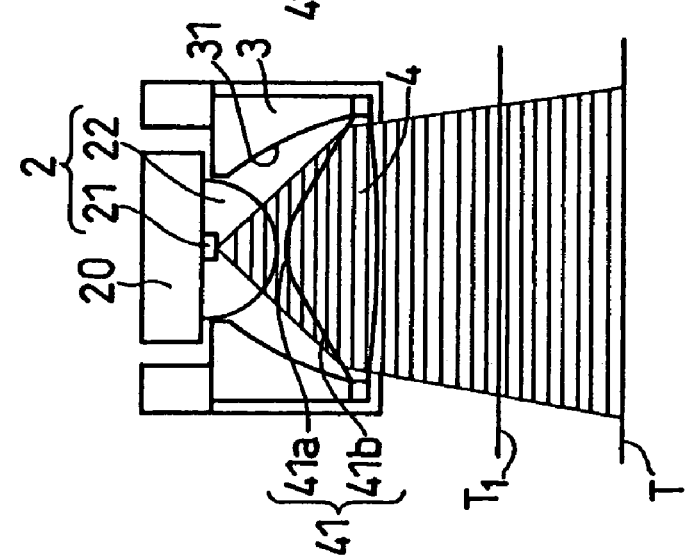

FIG. 5a, FIG. 5b and FIG. 5c are explanatory views in which the light irradiation pattern shown in FIG. 4a is decomposed. FIG. 5a shows a pattern in which the light is directly entered in the lens 4 from the luminous body 2 (light emitting element 2), transmitted, refracted and emitted, FIG. 5b shows a pattern in which light is reflected on the reflective surface 31 of the annular reflective member 3, entered in the lens 4, transmitted, refracted, and emitted, and FIG. 5c shows when both patterns are occurred (actual irradiation pattern).

As shown in FIG. 5a, the beam which enters in and emitted from the center 41a formed spherical with a small curvature radius among the light directly entering into the lens 4 from the luminous body 2 becomes a condensed one with uniform light volume at the area to be irradiated in the irradiation area (for example, the tooth surface T). Further, the light entering into the inclined face of the surrounding area 41b is uniformly refracted and emitted therefrom and is condensed with a uniform light volume on the tooth surface T.

The beam which is emitted from the luminous body 2, reflected on the reflective surface 31 of the annular reflective member 3 and is entered in the lens 4, transmitted, refracted and emitted therefrom is condensed with a uniform light volume on the surface T of the tooth as shown in FIG. 5b. The actual irradiation pattern in which both patters are overlapped like FIG. 5c becomes a irradiation pattern in which the illumination intensity per a unit area is large and uniform on the tooth surface T. Further, the irradiation energy of such irradiation pattern is not largely changed at the position T1 which is closer to the lens 4 than to the tooth surface T or more apart position. Therefore, irradiation light is uniformly acted from the surface to the deep portion and the hardening is progressed rapidly and homogenously for the prosthetic photo polymerization resin in the tooth.

Figure 6:
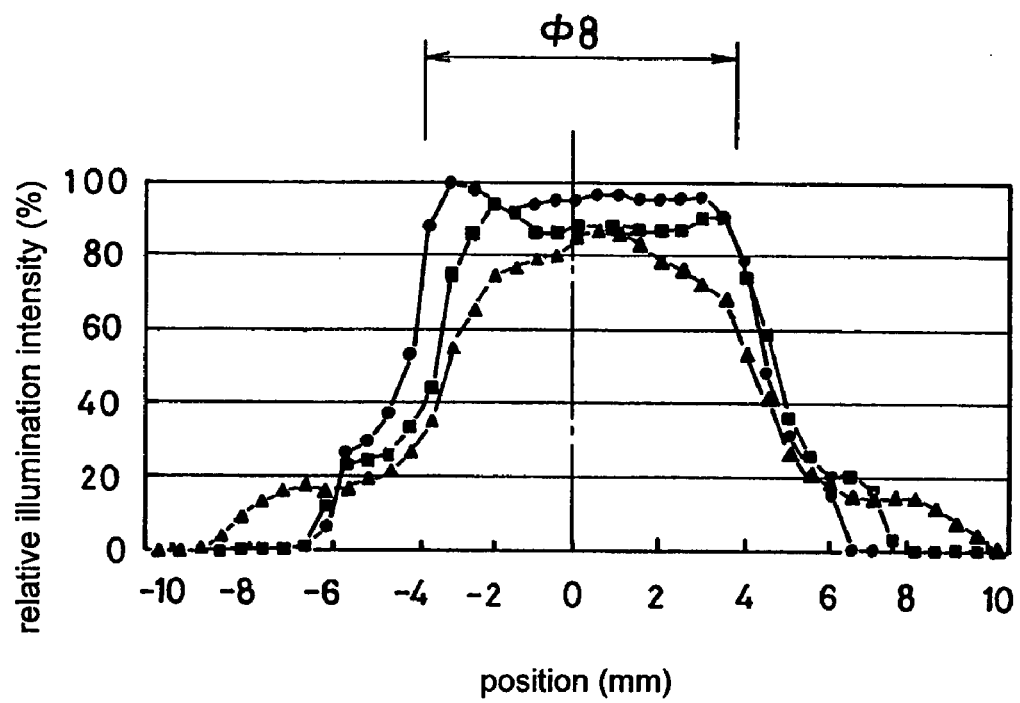

FIG. 6 shows the measured data of the relative illumination intensity (%) at the position of 5 mm distance from the light emitting end in case of FIG. 4a. The horizontal axis shows the distance from the optical axis (position is indicated as 0 mm) in the irradiation field, and the vertical axis shows the relative illumination intensity to the standard illumination intensity of the used light emitting element (LED chip). In the figure, it is understood that the illumination intensity which is uniform all over the irradiation field is obtained in the irradiation field of 8 mm diameter with an extremely high relative illumination intensity comparing with the area therearound. Thus, the irradiation light from the luminous body is usefully condensed on the irradiation field and a uniform and high irradiation energy is obtained, thereby achieving extremely rapid and high-quality resin hardening in case of hardening the prosthetic photo polymerization resin.

Figure 7A:
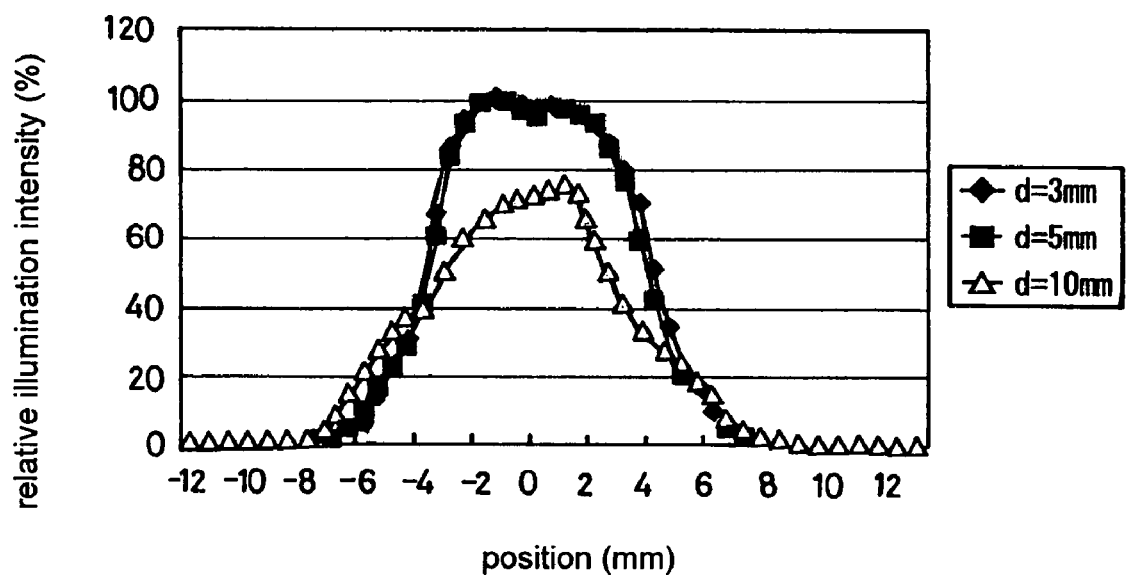
FIG. 7a and FIG. 7b show a graph of the measured data of the relative illumination intensity (%) based on the change in the distance from the light emitting end in case of FIG. 4a and FIG. 4b.
Figure 7B:
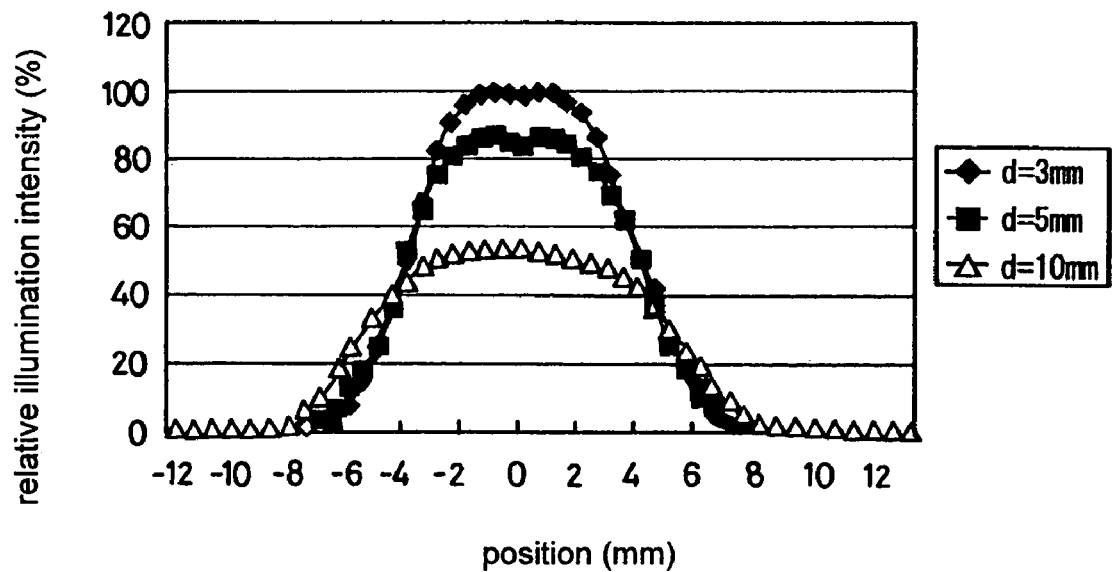

FIG. 7a and FIG. 7b respectively show a graph, similar to FIG. 6, showing the measured data of the relative illumination intensity (%) in the irradiation field when the distance from the light emitting end is changed when the embodiments in FIG. 4a and FIG. 4b are used. The reference "d" in the figure shows the distance from the light emitting end. As shown in the figures, the illumination intensity when "d" is 3 mm and 5 mm is high and uniform in the area of 8 nm diameter in the irradiation field. When "d" is 10 mm in FIG. 7a (the embodiment of FIG. 4a, namely the section of the reflective surface 31 of the annular reflective member 3 is concave), 30% of the illumination intensity is reduced. In case of FIG. 7b (the embodiment of FIG. 4b, namely the section of the reflective surface 31 of the annular reflective member 3 is convex), the illumination intensity is reduced by half. Accordingly, it is understood that, in case of the embodiment in FIG. 4a, the illumination intensity isn't largely changed depending on the distance from the light emitting end.

As mentioned above, the shape of the reflective surface 31 of the annular reflective member 3 and the shapes of the light entering end and the light emitting end of the lens 4 are associated with each other and a suitable irradiation pattern for hardening the prosthetic photo polymerization resin is obtained. The shape of the light emitting end of the lens 4 flat or convex, substantially flat, is formed so as not to cause trouble in the oral cavity and is desirably applied.

Further, if the light entering side and/or the light emitting side of the lens 4 made of glass is coated with an anti-reflection film mainly composed of magnesium fluoride, useless reflection is reduced and the light transmittance is improved, thus easily obtaining the light volume required for photo polymerization. In addition, the light entering side and/or the light emitting side of the lens 4 is provided with a water and oil repellent coating, or a water and oil repellent material is mixed with the lens material, contamination with prosthetic photo polymerization resin, saliva or oil isn't rarely caused when used in the oral cavity. The water and oil repellent coating agent is for example an oxidized mixture of which the main material is perfluoroaxialsilane (coating material using perfluoroalkyl such as perfluoro alkyl silane), silica, alumina and the like. The above-mentioned contamination is carried out with those processing, further, the refractive index or the light transmittance of the lens are improved and the lens is hardly damaged, thereby being extremely effective.

Figure 8A:
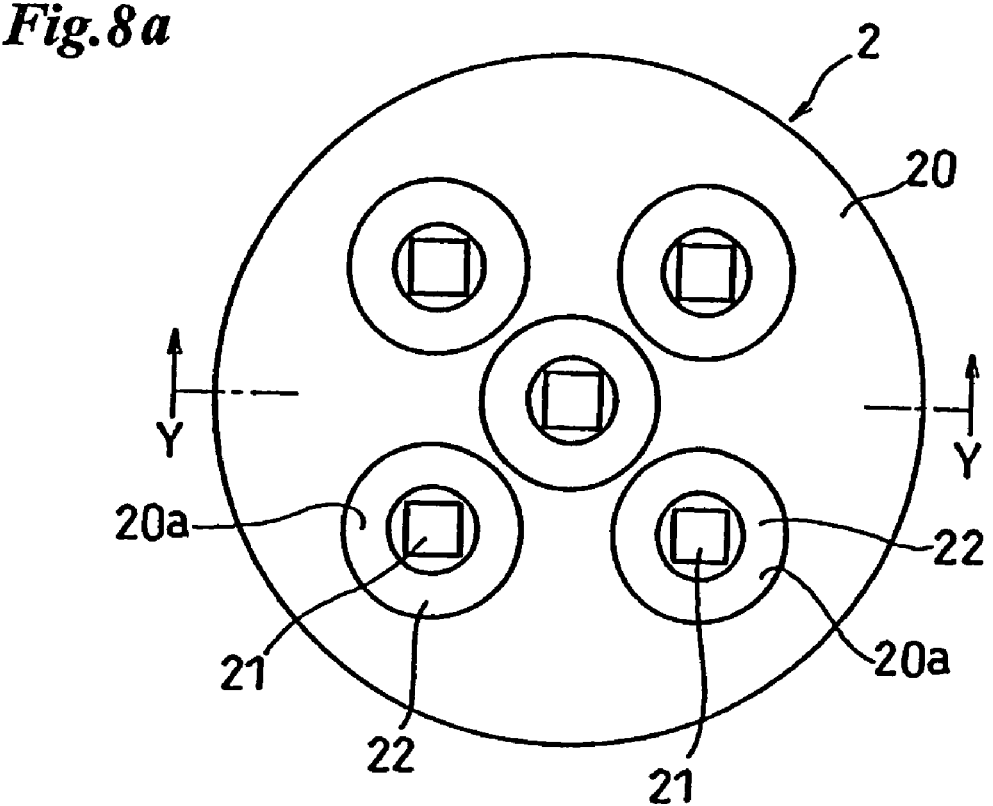
FIG. 8a and FIG. 8b show other embodiment of luminous body.
Figure 8B:
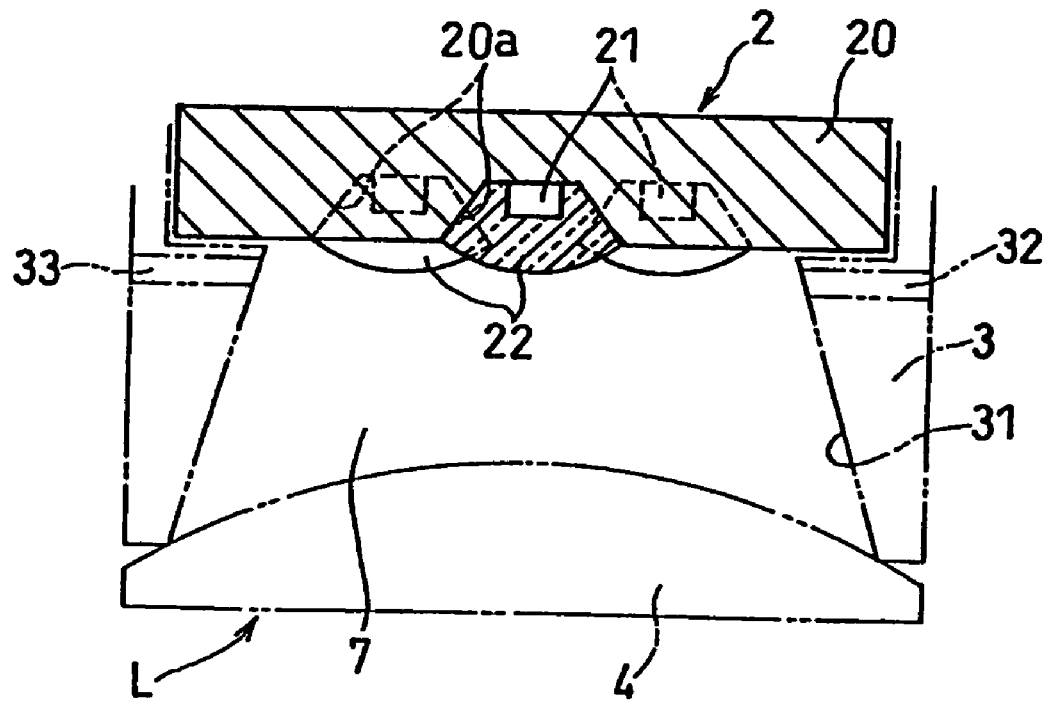
Figure 9:
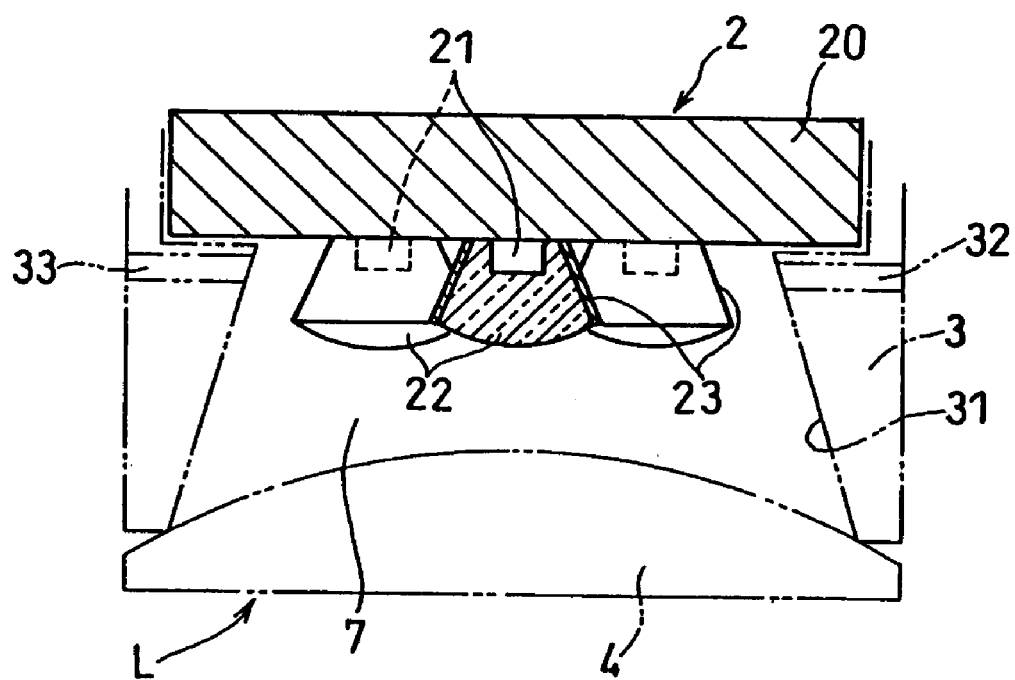
FIG. 9 shows the vertical section along the line Y-Y of a modified embodiment.

FIG. 8a and FIG. 8b show other embodiment of the luminous body 2, FIG. 8a shows its plane view and FIG. 8b shows the vertical section along the line Y-Y in FIG. 8a. FIG. 9 shows the vertical section along the line Y-Y of a modified embodiment. In FIG. 8a and FIG. 8b, five mortar-shaped concave parts 20a . . . are formed on the substrate 20 and the light emitting element 21 . . . is provided at the bottom of each one of the concave parts 20a . . . . Transparent resin is filled in each concave part 20a . . . to embed the light emitting elements 21 . . . and a resin mold 22 is formed respectively.

The luminous body 2 is combined with the annular reflective member 3 and the lens 4 to form the luminous unit L as shown in FIG. 8b. The inside of the concave part 20a is desirably mirror finished or evaporation finished with silver, thereby the lateral radiation light from the light emitting element 21 is usefully reflected and condensed and the outgoing light from the lens 4 becomes uniform with a large illumination intensity per a unit area in cooperation with the functions of the annular reflective member 3 and the lens 4. If a part of the plural light emitting elements 21 . . . is white light. LED (for example the light emitting element 21 at the center) and others are blue LED, the while light. LED is used for lightening the teeth and the blue LED is used for hardening the photo polymerization resin. Two functions are used with one irradiation apparatus by switching operation, thereby being convenience. Otherwise, it is possible that all of the plural light emitting elements 21 . . . is blue LED for hardening the photo polymerization resin or all of them is white light LED, wherein they may be selectively used such that the former is exclusively used for hardening the photo polymerization resin and the latter is exclusively used for irradiation.

If plural light emitting elements 21 with different output wavelength are provided, there exist light emitting elements with wavelength capable of hardening each resin contained in the photo polymerization resin material including plural kinds of resin of which the wavelength to be hardened is different, thereby completely hardening the photo polymerization resin material.

In FIG. 9, small cup members 23 . . . are provided on the surface of the substrate 20, a light emitting element 21 . . . is provided at the bottom of each small cup member 23 . . . , constituting like a collimator. Each cup member 23 . . . is filled with a transparent resin so as to embed the light emitting element 21 . . . and is formed with resin mold respectively, and the inside thereof is mirror finished or evaporation finished with silver. Other structures are the same as the embodiment in FIG. 8b and their functions are also the same, so that the common members have the same reference numerals and their explanations are omitted here. The luminous body 2 in FIG. 8 and FIG. 9 is only one example, and other constructions are not excluded.

In case of light emitting element like LED chip as shown in these embodiments, it may slightly include the light (for example, infrared light) with wavelength other than a desired wavelength (for example, the above-mentioned wavelength in case of blue LED). If the infrared light is contained, it may contribute heat generation, so that a suitable filter is desirably provided to remove the infrared light. Otherwise, an aperture (diaphragm) may be provided in order to reduce diffusion of the irradiation light from the luminous body.

Figure 10:
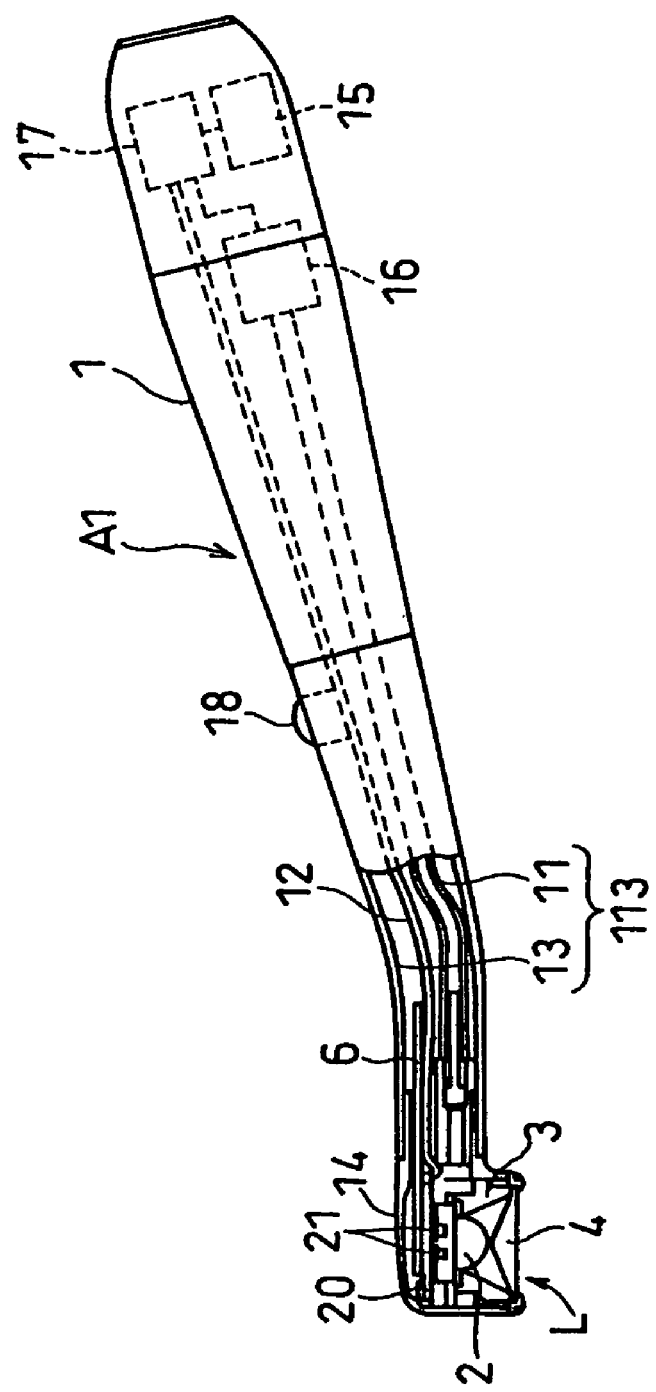
FIG. 10 is a partially broken appearance of one embodiment of a cordless type dental photo polymerization apparatus.

FIG. 10 is a partially broken appearance of one embodiment in which the handpiece type dental photo polymerization apparatus A is a cordless type dental photo polymerization apparatus A1. Power source (battery) 15, a fan 16, a control part 17 are housed in the handpiece body 1 and the base end of the air supply pipe 11 is connected to the air supply port of the fan 16. The control part 7 is connected to the power cord 12 for the luminous body and the fan 16 and the power source 15 is connected to the control part 17.

A handy switch 18 is provided on the perimeter of the handpiece body 1 and when the switch 18 is operated, the power source 15 is driven as a driving source to execute on and off operation of the luminous body 2 and the fan 16 by the control part 17. The exhaust pipe 13 is formed with the space in the handpiece body 1 as mentioned above, the cooling gas flowing in the exhaust pipe 13 is designed to be exhausted out of the apparatus from the base end of the handpiece 1. Other structures are the same as the dental photo polymerization apparatus A shown in FIG. 1, so that the common members have the same reference numerals to omit their explanation.

Figure 11:
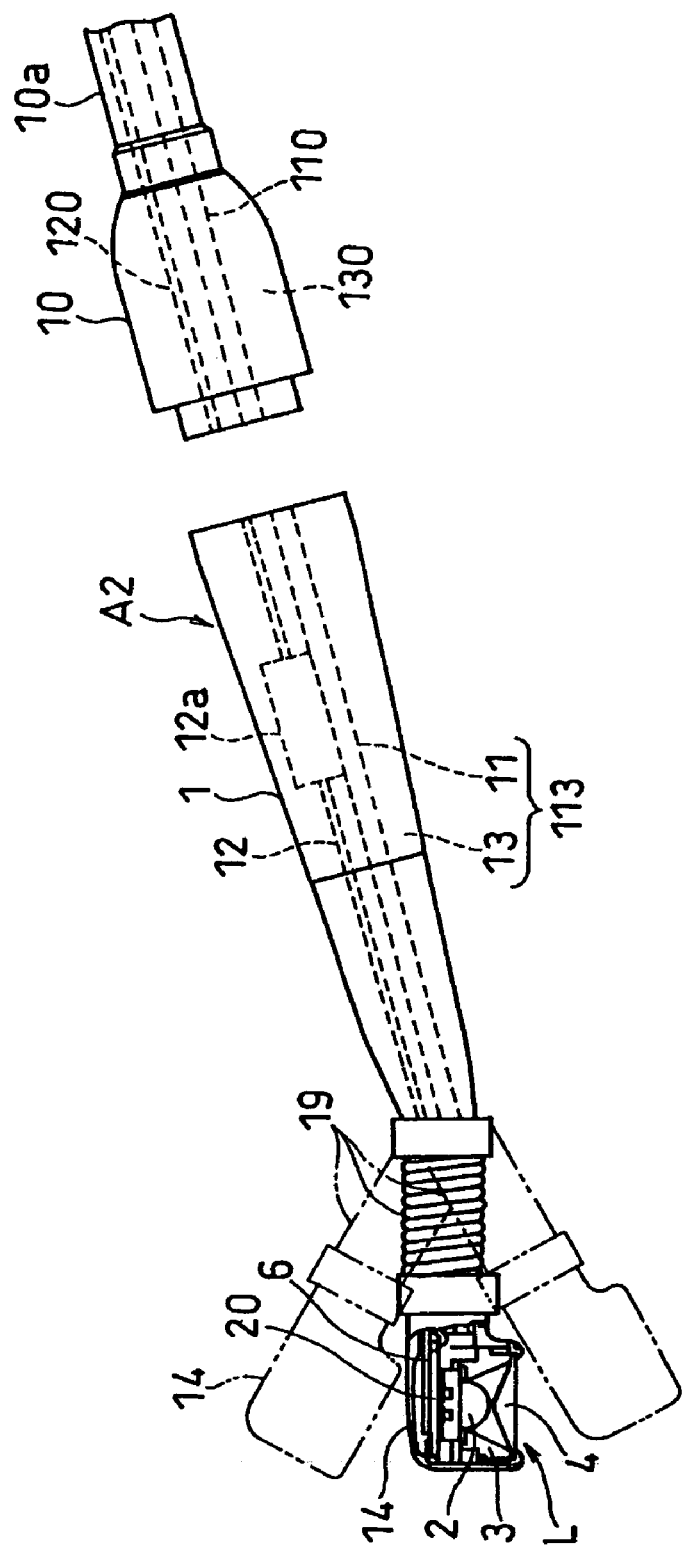
FIG. 11 is a partially broken appearance of a modified embodiment of a cordless type dental photo polymerization apparatus in FIG. 1.

According to the dental photo polymerization apparatus A2 shown in FIG. 11, the tip portion of the handpiece body 1 is constructed with a flexible member 19. The flexible member 19 has such flexibility that it is bent with a hand and it keeps the bent condition as shown in two-dotted lines in the figure. Therefore, an operator bends the flexible member 19 at a preferable angle depending on the position or angle of the target region to be irradiated and irradiates light at a desirable direction from the light outlet 14, thereby improving treatment accuracy. It goes without saying that the flexible member 19 may be applied to the cordless type apparatus shown in FIG. 9. Other structures are the same as the embodiment shown in FIG. 1, so that the common members have the same reference numerals to omit their explanation.

Figure 12:
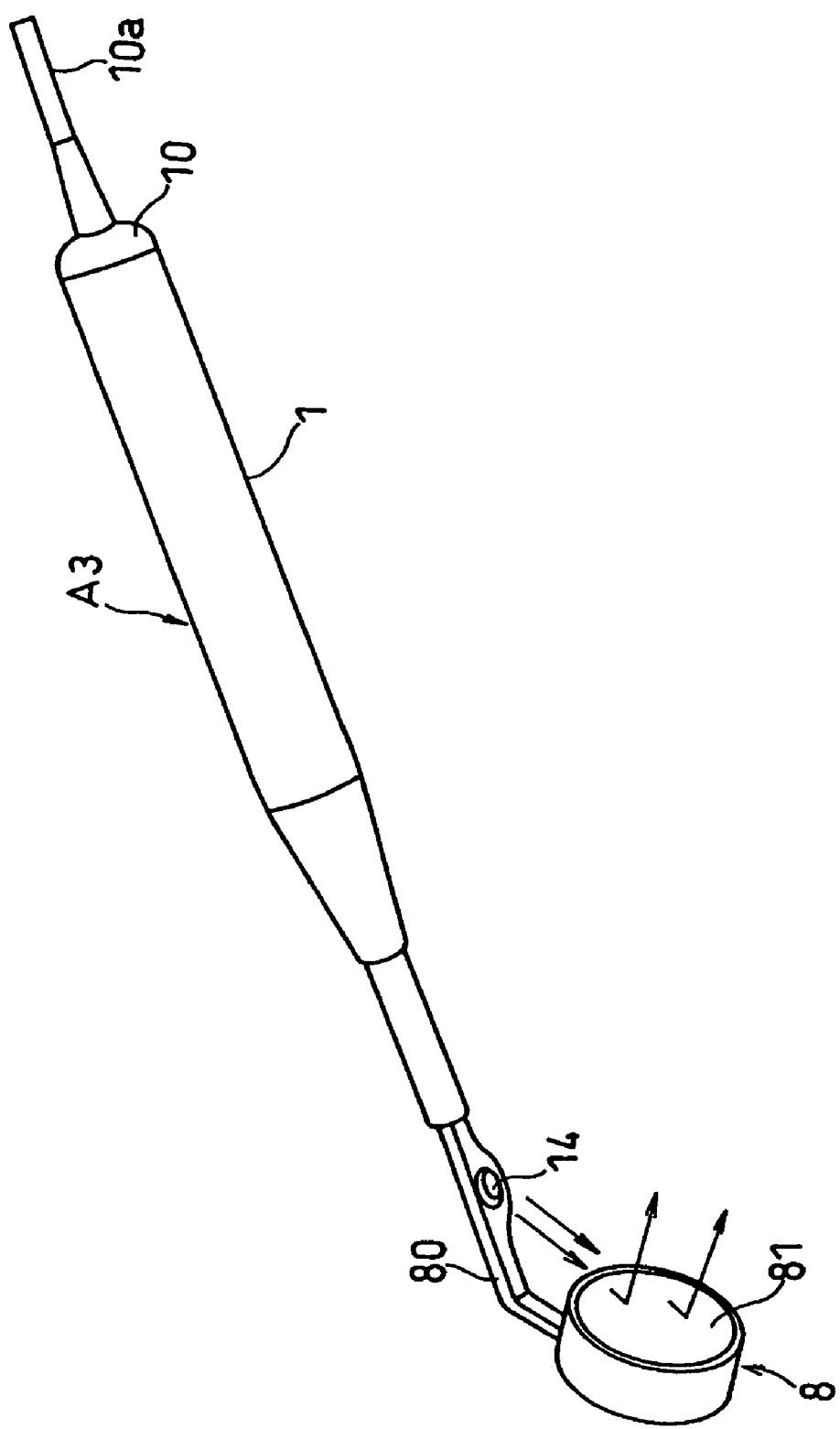
FIG. 12 shows an outline view of a mirror type dental photo polymerization apparatus.

The embodiment in FIG. 12 is a mirror type dental photo polymerization apparatus A3. A dental mirror 8 is provided at a suitable angle at the tip end portion of the handpiece body 1 and the light outlet 14 as mentioned above is formed at the base of a support body 80 of the dental mirror 8. The light emitting direction from the light outlet 14 is a mirror surface 81 of the dental mirror 8 and the outgoing light is reflected on the mirror surface 81 to be irradiated on the region to be irradiated as shown in the figure. An operator can execute hardening of the prosthetic photo polymerization resin by irradiating the light from the light outlet 14 on the region to be irradiated while watching the reflected image of the region to be irradiated (tooth) on the mirror surface 81 like a general dental mirror.

In the embodiment of FIG. 12, the luminous unit L as mentioned above is incorporated into the light outlet 14 and the handpiece body 1 includes the air supply pipe 11, the power cord 12, and the exhaust pipe 13 as mentioned in the above embodiments. Further, like the embodiments in FIG. 1 and FIG. 11, the handpiece base 10 as a coupling is detachably connected to the base end of the handpiece body 1, the hose 10a including the air supply pipe 110, the power cord 120 and the exhaust pipe 130 is connected to the handpiece base 10. It goes without saying that the dental photo polymerization apparatus 3A may be a cordless type as shown in FIG. 10.

In the embodiment of FIG. 12, the light from the light outlet 14 is directed to the mirror surface 81, however, the light may directly irradiate the region to be irradiated from the light outlet 14. Further, plural luminous units may be arranged so as to surround the mirror surface 81 of the dental mirror 8 to constitute the light outlet 14. Or the dental mirror 8 may be detachable to the handpiece body 1.

Figures 13A, 13B:
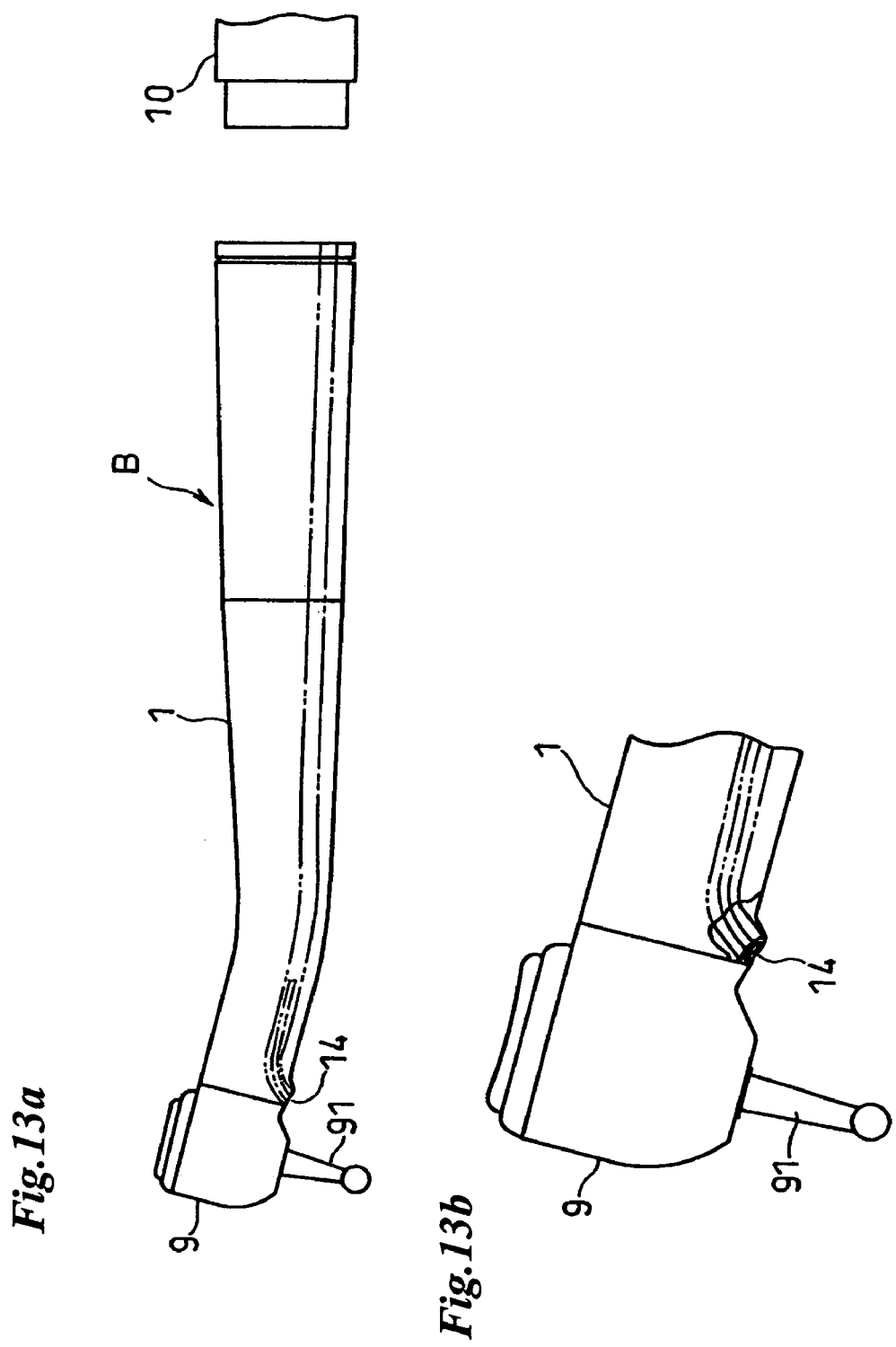
FIG. 13a and FIG. 13b show a dental irradiation apparatus wherein a lighting function is provided for a dental air turbine handpiece or a dental micro motor handpiece.

FIG. 13a and FIG. 13b show a dental irradiation apparatus B wherein a lighting function is provided for a dental air turbine handpiece or a micro motor handpiece, or the internal state of the patient is observed by the fluorescence excited by the irradiation light or the reflection light. The light outlet 14 is provided at the neck of a head 9 to which a cutting tool 91 for teeth is attached and the light emitting direction from the light outlet 14 is around the tip end portion of the cutting tool 91. The light outlet 14 is constructed similar to the above-mentioned embodiments and the handpiece body 1 includes the air supply pipe, the exhaust pipe, the cooling means comprised of a heat sink and the like other than the cutting tool driving means and the working medium supply pipe like a general air turbine handpiece or micro motor handpiece.

White light is irradiated from the light outlet 14 in the present embodiment to be served as a light for the treatment region. An operator can drive the cutting tool 91 to cut a tooth while irradiating on the tooth from the light outlet 14. The reference numeral 10 is a handpiece base as a coupling and is connected with a hose (not shown) including the pipe for cooling the luminous body and the power cord as mentioned above, other than the acting medium supply pipe and the power cord for driving the cutting tool. It goes without saying that they are connected to the corresponding pipes in the handpiece body 1 when the base portion 10 is connected to the base end of the handpiece body 1.

Figure 14:
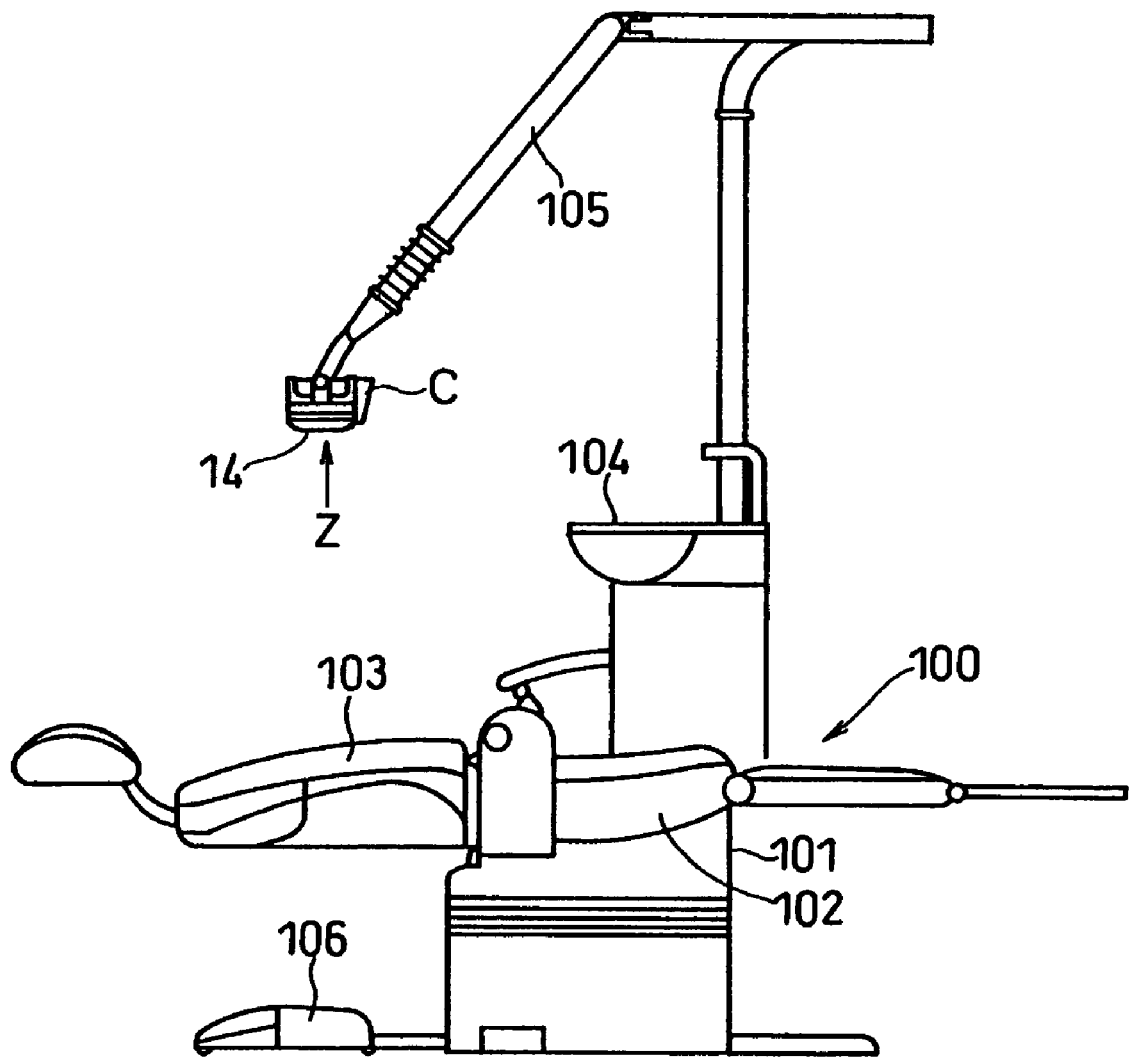
FIG. 14 shows an appearance of an embodiment in which the medical irradiation apparatus of the present invention is applied to a dental light provided for a dental treatment apparatus.
Figure 15A:
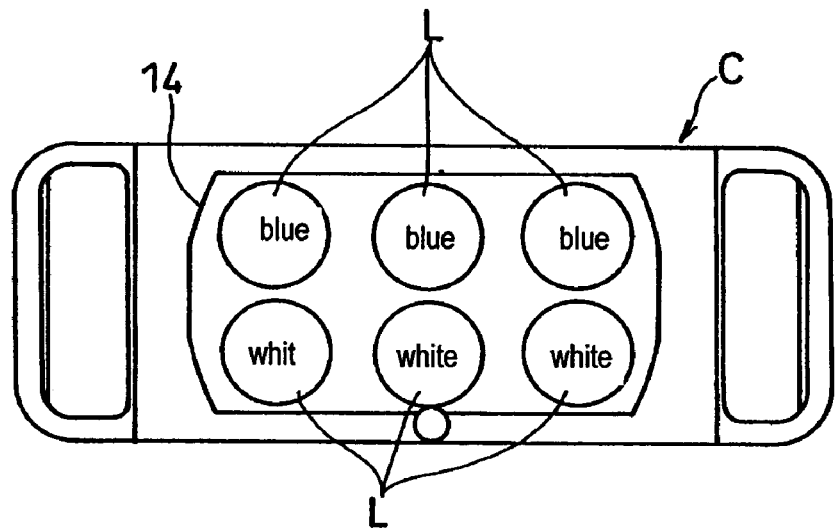
FIG. 15a is a fragmentary view in Z direction in FIG. 14
Figure 15B:
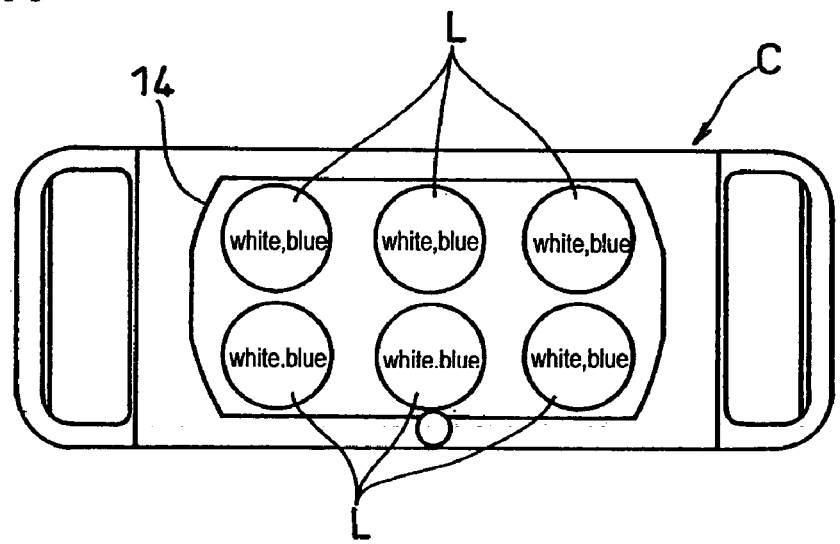
FIG. 15b shows its modification.

FIG. 14 shows an embodiment in which the medical irradiation apparatus of the present invention is applied to a dental light (shadowless light) provided for a dental treatment apparatus. FIG. 15a is a fragmentary view in Z direction in FIG. 14 and FIG. 15b shows its modification. In FIG. 14, the reference numeral 100 indicates a treatment bed constructed such that a seat board 102 is supported on the basement 101 so as to be movable up and down and a back board 103 is inclinably connected to one end of the back board 103. The reference numeral 104 is a gargle spittoon provided at the side of the dental treatment bed 100. The reference numeral 105 is a hanger arm supporting the dental light C as the medical irradiation apparatus of the present invention so as to be vertically moved and horizontally rotated. The reference numeral 106 is a foot switch for turning on and off of elevation and inclination of the treatment bed 100 and several handpieces.

On the dental treatment bed 100, the oral cavity of the patient lying face up thereon is irradiated with the dental light C. In FIG. 15a, six luminous bodies L . . . are incorporated in the light outlet 14 and the light emitting element is blue LED chip at the upper row and is white LED chip at the bottom row. In this embodiment, switching operation is executed such that the luminous units L . . . at the lower row are turned on for irradiating the oral cavity like a general shwadowless light, and the luminous units L . . . at the upper row are turned on for hardening the prosthetic photo polymerization resin in the tooth.

The embodiment in FIG. 15b is provided with a blue LED chip and a white LED chip per each luminous unit L . . . and the switching operation mentioned above is executed by on-off switching control of the blue LED chip and the white LED chip per each luminous unit L . . . to be used for lighting in the oral cavity or for hardening the prosthetic photo polymerization resin. Although it is not shown in the figure, the cooling medium mentioned above is preferably provided in the light outlet 14. The cooling pipe, the power cord for the luminous body and the like are connected to the compression air source and the power source provided around the dental treatment bed 100 via the hanger arm 105, and the compression air source and the power source may be selectively incorporated in the dental light C.

In the above-mentioned embodiments, the present invention is applied to a dental irradiation apparatus, however, it may be applied to other medical fields. Further, the light outlet 14 may be formed planular to improve the operability in the oral cavity and its shape may be suitably selected. Although a cooling air and a heat sink are applied as a cooling means, peltier element may be used.

The invention claimed is:

1. A medical irradiation apparatus comprising:
a main body;
a luminous body comprised of a light emitting element provided in a light outlet of said main body;
an annular reflective member with an annular reflective surface provided at the circumference of said luminous body, said reflect surface reflecting the light from said luminous body forward; and
a lens member provided so as to cover a forward opening of said reflective member, said lens member refracting and transmitting the direct light from said luminous body and the light reflected from said reflective member, whereby
almost all the outgoing light from said lens member is emitted so as to direct into a specified irradiation area, and wherein
said specified irradiation area is defined substantially as a cylindrical area around an optical axis of outgoing light where the distribution of illumination intensity is substantially uniform in a field area of each irradiation field orthogonal to the optical axis and the illumination intensity is substantially the same in said cylindrical irradiation area;
said lens member is comprised of a lens which is rotationally symmetrical around its center axis;
a light entering side of said lens is formed convex and a light emitting side of said lens is formed convex or substantially flat;
said lens member has a light entering side which is composed of a curved surface at a center and continuous inclined surfaces therearound; and
said curved surface is spherical with a small curvature radius, whereas said inclined surface is substantially linear in a section including a central axis of said lens member.

2. A medical irradiation apparatus comprising:
a main body;
a luminous body comprised of a light emitting element provided in a light outlet of said main body;
an annular reflective member with an annular reflective surface provided at the circumference of said luminous body said reflect surface reflecting the light from said luminous body forward; and
a lens member provided so as to cover a forward opening of said reflective member, said lens member refracting and transmitting the direct light from said luminous body and the light reflected from said reflective member, whereby
almost all the outgoing light from said lens member is emitted so as to direct into a specified irradiation area, and wherein
said specified irradiation area is defined substantially as a cylindrical area around an optical axis of outgoing light where the distribution of illumination intensity is substantially uniform in a field area of each irradiation field orthogonal to the optical axis and the illumination intensity is substantially the same in said cylindrical irradiation area;
a cooling means having an air supply pipe for supplying air in a space area surrounded with said luminous body, said reflective member, and said lens member and having an exhaust pipe for exhausting the air from said space area.

3. The medical irradiation apparatus as set forth in claim 1 or 2, wherein said annular reflective member is formed as a rotationally symmetrical shape around its center axis, and wherein said reflective surface is formed in such shape that its distal opening for irradiation is more enlarged than a base portion thereof.

4. The medical irradiation apparatus as set forth in claim 1 or 2, wherein the section of said reflective surface along its center axis is linear.

5. The medical irradiation apparatus as set forth in claim 1 or 2, wherein the section of said reflective surface along its center axis is concave.

6. The medical irradiation apparatus as set forth in claim 5, wherein the shape of said reflective surface is defined by an oval arc.

7. The medical irradiation apparatus as set forth in claim 5, wherein the section of said reflective surface along its center axis is defined by a bended line which is composed of continuous plural straight lines.

8. The medical irradiation apparatus as set forth in claim 1 or 2, wherein the section of said reflective surface along its center axis is convex.

9. The medical irradiation apparatus as set forth in claim 8, wherein the shape of said reflective surface is defined by parabola and wherein said parabola is defined as such one that the tangent lines to the points where said annular reflective member and said lens member are jointed overlap to accord with the most external optical path line from said luminous body among all the optical path lines of the light directly pointed to said lens from said luminous body, which define direct irradiation area of said luminous body.

10. The medical irradiation apparatus as set forth in claim 1 or 2, wherein said reflective member and said lens member are detachable to said light outlet by means of a screw type cap member, by which their airtightly attachment to said light outlet is performed via an O-ring.

11. The medical irradiation apparatus as set forth in claim 1 or 2, wherein said main body constitutes a handpiece which is held and handled with a hand or finger and wherein said light outlet is formed at the tip end portion of said main body.

12. The medical irradiation apparatus as set forth in claim 11, wherein said handpiece comprises a main body to which a base portion is detachable.

13. The medical irradiation apparatus as set forth in claim 1, wherein said apparatus is constructed as a cordless type in which a power source and a control part are contained in said main body.

14. The medical irradiation apparatus as set forth in claim 1 or 2, wherein said light emitting element is a bear chip.

15. The medical irradiation apparatus as set forth in claim 14, wherein said bear chip is molded with a transparent resin.

16. The medical irradiation apparatus as set forth in claim 1 or 2, wherein said light emitting element is comprised of an integrated wafer provided with plural bear chips on a substrate.

17. The medical irradiation apparatus as set forth in claim 16, wherein said bear chip is molded with a transparent resin in its light emitting side.

18. The medical irradiation apparatus as set forth in claim 1 or 2, wherein said light emitting element is such one that it radiates light with specific wavelength suitable for hardening a photo polymerization resin.

19. The medical irradiation apparatus as set forth in claim 1 or 2, wherein said light emitting element radiates a white light.

20. The medical irradiation apparatus as set forth in claim 1 or 2, wherein said luminous body is comprised of a light emitting element for radiating light with specific wavelength suitable for hardening a photo polymerization resin and of a light emitting element for radiating a white light.

21. The medical irradiation apparatus as set forth in claim 1 or 2, wherein said specified irradiation area is a space area where the distance from a light emitting end of said light outlet is 1 to 12 mm and whose irradiation field diameter is 5 to 12 mm.

22. The medical irradiation apparatus as set forth in claim 1 or 2, wherein said light entering side and/or light emitting side of said lens member is coated with an anti-reflection film.

23. The medical irradiation apparatus as set forth in claim 1 or 2, wherein said light entering side and/or light emitting side of said lens member is coated with a water repellent or oil repellent coating.

24. The medical irradiation apparatus as set forth in claim 2, wherein an air supply communication bore for communicating between said air supply pipe and said space area and an exhaust communication bore for communicating between said space area and said exhaust pipe are further provided in said reflective member, whereby a cooling gas from said air supply pipe is introduced in said space area via said air supply communication bore and is exhausted from said exhaust pipe via said air exhaust communication bore.

25. The medical irradiation apparatus as set forth in claim 2, wherein a heat sink is further provided in a back of a support body of said luminous body and wherein the back of the support body and the heat sink are disposed in said exhaust pipe.

26. The medical irradiation apparatus as set forth in claim 25, wherein said support body is constructed by a substrate of said light emitting element.

27. The medical irradiation apparatus as set forth in claim 2, wherein said air supply pipe is connected at a base portion to an air supply means provided in said main body.

28. The medical irradiation apparatus as set forth in claim 2, wherein said air supply pipe is connected at a base portion to an air supply means provided outside of said main body.

29. The medical irradiation apparatus as set forth in claim 2, wherein said apparatus is a such cordless type that that a power source and a control part are contained in said main body and that drive control of said light emitting element and said air supply means is executed by means of said power source and said control part.

* * * * *